United States Patent [19]

Urso

[11] Patent Number: 4,586,521
[45] Date of Patent: May 6, 1986

[54] MULTI-MOTION DENTAL FLOSSER

[76] Inventor: Charles L. Urso, 215 Newton St., Waltham, Mass. 02154

[21] Appl. No.: 558,826

[22] Filed: Dec. 7, 1983

[51] Int. Cl.$^4$ ............................................. A61C 15/00
[52] U.S. Cl. ................................................... 132/92 R
[58] Field of Search ................................ 132/92 R, 91

[56] References Cited

U.S. PATENT DOCUMENTS

| | | | |
|---|---|---|---|
| 3,759,274 | 9/1973 | Warner | 132/92 R |
| 4,326,549 | 4/1982 | Hinding | 132/92 R |
| 4,327,740 | 12/1981 | Florindez et al. | 132/92 R |
| 4,458,702 | 6/1984 | Grollimund | 132/91 |

Primary Examiner—Robert Peshock

[57] ABSTRACT

A dental hygiene device for cleaning between teeth wherein dental floss is advanced, across a span between the tines of a fork, to a motorized level-winding take-up spool. The fork is reciprocated by the motor, resulting in two-dimensional movement of the floss within the span. The moving fork is shielded to prevent contact with oral tissues. Motor speed is varied by a potentiometer operated by way of a trigger. The floss span can be held taut, during passage between tightly contacting teeth, by a brake operated by way of the trigger. An adjustable drag connected to a contamination protected dispensing spool controls floss tension.

10 Claims, 5 Drawing Figures

MULTI-MOTION DENTAL FLOSSER

BACKGROUND

Cleaning the surfaces between adjacent teeth generally is a special problem outside the dental office. Those areas are not accessible to a tooth brush, yet they must be cleaned regularly. The consequence of not removing deposits there, especially on tooth surfaces inside the free gingiva, will very likely lead to diseases affecting teeth and periodontal tissues. The latter accounts for the large percentage of people who lose their natural teeth.

A cause of periodontal disease is initiated by bacteria acting on food particles deposited on tooth surfaces inside the gingival sulcus. The deposits become plaque which later harden as a result of calcium deposition. As additional debris accumulate, a sequence of biological, physical, and biochemical events occur which eventually lead to destruction of previously healthy tissues.

A cleaning method supplementary to brushing is therefore necessary. Good results have come from the use of dental floss or tape held and manipulated with the hands. Floss or tape tensioned within various types of frames which are manipulated with the hands can also produce positive results. However, these techniques require skill with considerable perserverance and are in the main, arduous and burdensome task.

Efforts to reduce the flossing burden have produced some complex devices that are patented. These include U.S. Pat. No. 3,534,745 which reveals a device that has dental tape spanned between two prongs which form a U-shape. The device moves the prongs such that the motion of the tape they hold generates a shape envisioned as two cones attached at their apices. Included in the device are supply and take-up reels disposed to provide replacement for the spanned tape increment by manual advancement when desired by the user.

U.S. Pat. No. 4,014,354 describes a device that holds a length of floss between two spaced L-shaped arms. The device reciprocates the arms and the floss in an arc about the axis of a handle to which one end of the arms are attached.

In the interests of comfort, neither of the above mentioned devices show means to protect the oral tissues from contact with the powered motion of the prongs or support arms. Nor can they automatically replace the used floss.

U.S. Pat. No. 3,667,483; U.S. Pat. No. 3,759,274; U.S. Pat. No. 3,847,167; U.S. Pat. No. 4,326,549 and U.S. Pat. No. 4,338,957 disclose devices that reciprocate floss or tape in only one dimension; in a transverse motion across the tooth surface. The vertical cleaning motion must be manually provided by the user.

DISCLOSURE OF THE INVENTION

The multi-motion dental flossing device disclosed herein has important advantages over the aforementioned closest prior art. It can impart a two dimensional flossing motion flush against the dentition surfaces. Specifically, the floss reciprocates vertically on the tooth while constantly changing floss surface by simultaneously moving in a transverse direction. The continual horizontal feeding and replacement of floss with a clean dry surface, in concert with the rapid vertical oscillations, loosens the adhering material and carries off the freed particles in and on the used floss. This combination of actions is especially important on dentition surfaces inside the free gingiva; to dislodge deposits and carry the debris out of the sulci. The efficiency of this process cannot be matched by the prior disclosed flossing instruments. Since the transverse motion of the floss is relatively slow, the only rapid motion is substantially perpendicular to the gingival surface to which it comes in contact. Thus, there is no rapid sawlike motion across soft tissues; a safety consideration. Having a safer cleaning motion, the tool has the added potential for use as an interdental polisher when used with floss designed with, or in conjunction with, a fine abrasive material. The moving parts, excepting the floss, are shielded to prevent contact with the oral tissues of the user.

The instrument is easily loaded with a covered supply spool which inhibits floss contamination. It level-winds the retrieved floss to allow the use of compact spools. Level-winding also allows the management of a greater amount of floss per unit volume and reduces the frequency of spool changes.

After use, the oral portion of the instrument can be cleaned by simply rinsing under hot running tap water without having to remove parts. It can be stored with the spools in place.

BRIEF DESCRIPTION OF THE DRAWINGS

These and other details and advantages of my invention will be described in connection with the accompanying drawings, which are furnished only by way of illustration and not in limitation of the invention, and in which drawings.

DESCRIPTION OF THE MULTI-MOTION DENTAL FLOSSER

Figure 1:
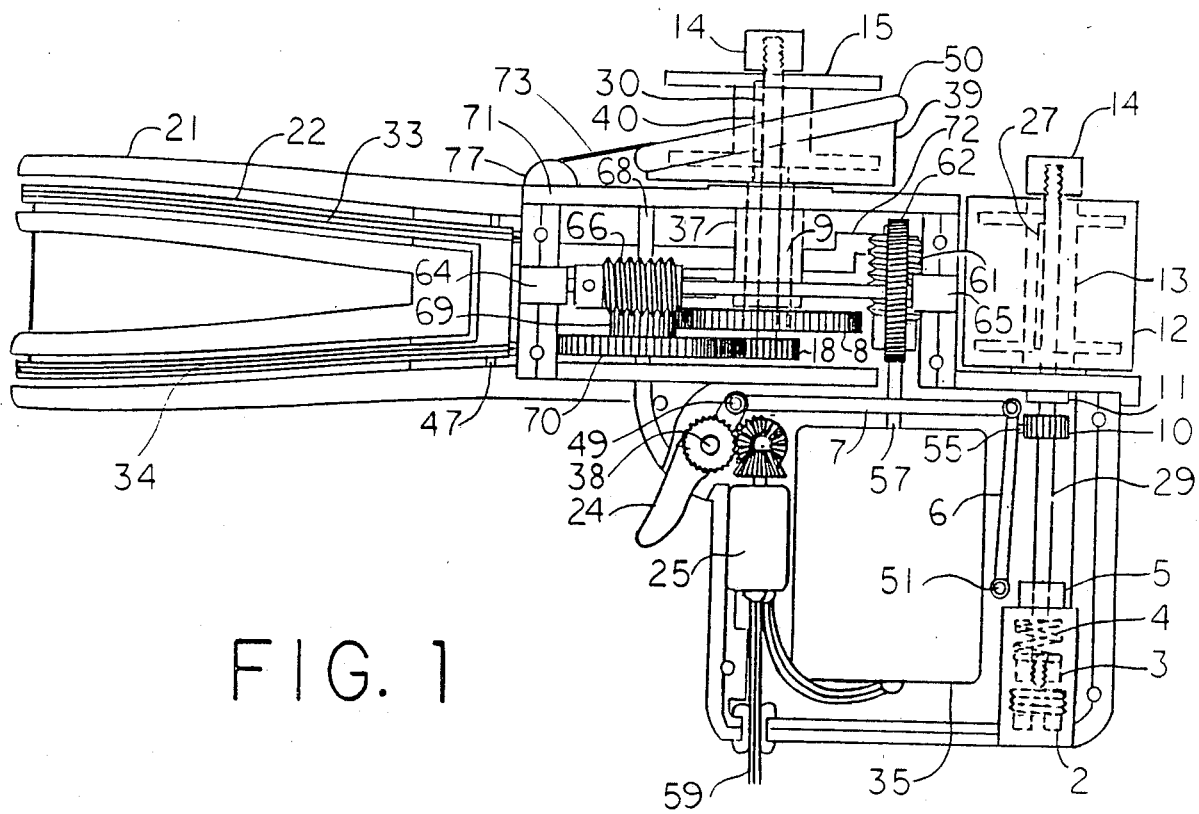
FIG. 1, in a top plan, illustrates the flossing device with the top cover of the gearbox removed and the handgrip cover removed.
Figure 2:
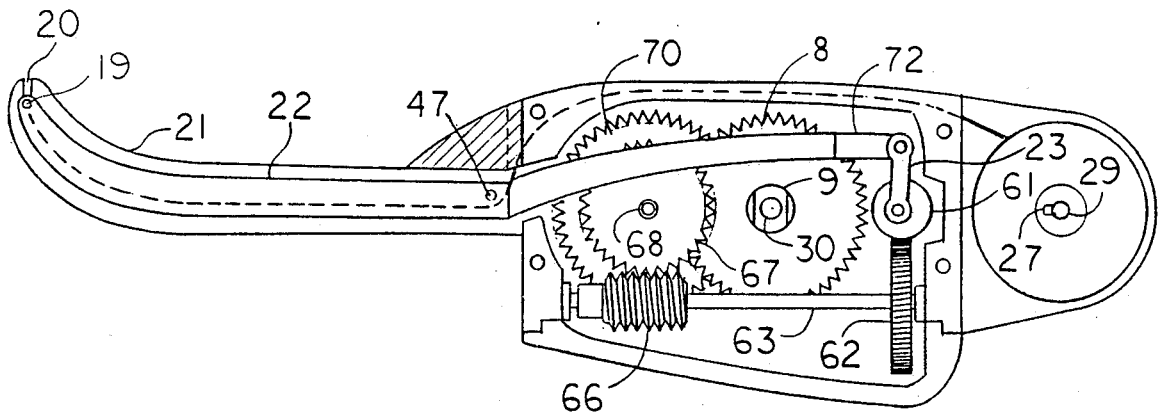
FIG. 2, is a side elevation view of the flossing device with parts removed which are: the outer half of a shield tine, the take-up spool and its retainer cap, the rail and its support cup, the side cover of the gearbox, and the dispensing spool retainer cap.

The dental flossing device 1 described herein and shown in the figures includes two symmetrical forks 80, 81; one within the other. In FIGS. 1 and 2, each tine 22 of the inner fork is flanked laterally and medially by each half of an outer shield fork tine 21 in a spaced sandwich arrangement. The inner fork 80 is disposed to reciprocate within the stationary shield fork 81 and though they are in close proximity, they do not contact each other. Extensions of the device housing 83 form the shield fork tines 21 which are larger than the inner fork tines 22.

The purpose of the shield fork 81 is to shield the reciprocating inner fork 80 and prevent the latter from directly contacting the oral tissues of the user. Slots 20 in both halves of each shield tine 21, as shown in FIG. 2, facilitate threading the eyelets 19 of the inner tines and allow passage and motion of floss that spans the inner tines 22.

Figure 3:
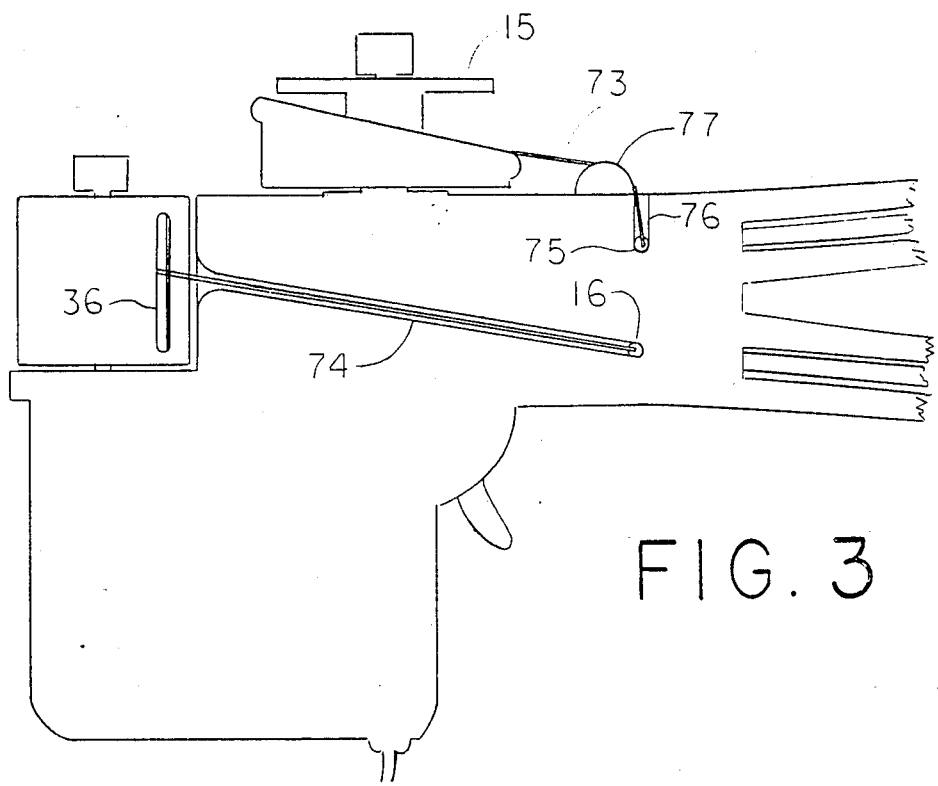
FIG. 3 is a partial bottom outline of the flossing device showing openings and grooves that guide the dental floss.

Shown in the figures is a plastic dispensing spool 13 on which is wound dental floss. A plastic shell 12 covers the dispensing spool to protect the floss from contamination. The spool 13 with its protective shell is mounted on the device by sliding it on a rotatable spindle shaft 29. A flat key 27 projects from the shaft and fits into a keyway in the spool hub to lock them together. The spool is held on the shaft by a threaded cap 14. A slot-like opening 36 in the shell wall 12 allows floss to be drawn from the spool as shown in FIG. 3.

A groove 74 in the housing of the device provides a route for the floss to pass from the dispensing spool 13 to an opening 16. After passing through the opening, the floss passes to groove 33 in a tine 22 of the inner fork (see FIGS. 1, 2, 3 and 5). The floss follows the groove which emerges on a lateral side of a distal portion of the tine to meet the opening of the eyelet 19. After passing through eyelet 19, the floss spans the fork to pass through the eyelet of the opposite tine to follow groove 34 back to an opening 75 in the housing. The floss then passes through an opening 75 and a guide groove 76, then over a guide 77 to a take-up spool 15. The take-up spool is loaded on a spindle shaft 30. A flat key 40 projects from the shaft and fits into a keyway in the spool hub to lock them together.

The take-up spool 15 is partially enclosed in a cylindrical cup 39 disposed to rotate about the spool on a common axis. the cup is coaxially fixed to a first bearing 9 in which a journaled portion of shaft 30 is coaxially mounted to rotate. A journaled portion of first bearing 9 is mounted to rotate within a larger second bearing 37. A first gear 18 is coaxially fixed to an end portion of shaft 30 and a second gear 8 is coaxially fixed to an end portion of bearing 9. The cup serves to support an elliptically shaped rail 50 positioned such that its elliptical center is located at the midpoint of the spool core axis. The minor axis of the ellipse is perpendicular to the spool axis. The major axis of the ellipse is tilted at an oblique angle to the spool axis. The angle is such that if each end of the spool core is assumed to be intersected by a plane, perpendicular to the spool axis, both vertices of the elliptical rail are located between the planes. Further, the closest distance from each plane to the closest point on the rail surface is approximately the diameter of the dental floss to be wound on the spool. The distance from the spool axis to the closest rail surface point is greater than the distance from the spool axis to the furthest point on the spool, including the furthest point on the maximum amount of floss to be wound on the spool. Thus, the cup and rail form a cam encircling the spool. The elliptical rail is constructed of a material that lends itself to produce low sliding friction (as many plastics and polished metals do) or it is coated with such a material.

The take-up spool 15 is driven by way of the spindle-shaft 30 and first gear 18, to take up floss 73. The cup and elliptical rail are driven, by way of first bearing 9 and second gear 8, to rotate about spool 15, at a slower rate than the spool rotation rate. The floss 73, drawn over the rotating elliptical rail 50, is guided by the angled rail to traverse the core of the spool and result in even-winding onto the spool core.

The preferred number of windings of dental floss in each successive layer on the spool core can be obtained by selection of a proper ratio of the rotational rate at which the spool is driven, to the rotational rate at which the elliptical rail is driven. The number relate in the following way:

number of windings per layer = rotational rate of the spool twice the rotational rate of the elliptical rail Both the take-up spool 15 and rail 50 are driven by an electric motor 35 by way of a speed reduction gear train shown in FIGS. 1 and 2. The gear train drives the take-up spool 15 at a slow rotation rate and the rail 50 at a slower rate (preferred rates are determined by standard gear speed formulae). Fixed to the motor shaft 57 is a first worm 61 which rotates a third gear 62. The gear 62 is fixed to a first shaft 63 which is mounted to rotate within bearins 64 and 65. Also fixed to shaft 63 is a second worm 66 which rotates a fourth gear 67. That gear is fixed to a second shaft 68. A fifth gear 69 and sixth gear 70 are also mounted and fixed to the second shaft. The shaft 68 is mounted to rotate within two bearings (not shown), one of which is inserted into the device housing and the other is inserted into a gearbox side cover 71. When gear 67 is driven by worm 66, gears 69 and 70 drive gears 8 and 18 to rotate the rail 50 and the take-up spool 15, respectively.

Pivotally connected to an end of worm 61 is an end portion of a connecting rod 23 (FIG. 2). The connection is made by way of a pin eccentrically inserted into the worm end, thus forming an operative crank with a connecting rod. An opposite end portion of the connecting rod is pivotally connected to an end portion of a lever 72. The opposite end of the lever is rigidly connected to the inner fork as shown in the figures. Thus, as worm 61 rotates, it imparts reciprocating motion to the distal working end of the fork by pivoting the lever and fork about a pivot pin 47. Simultaneously, the worm sets the gear train in motion to level-wind retrieved dental floss.

The electric motor 35 derives its power from a power means (batteries or AC, fed through a conductor wire 59) mediated by a potentiometer 25. A trigger 24 is connected to the control shaft of the potentiometer by way of the simple gear train indicated in FIG. 1.

They are situated such that when finger pressure moves the trigger, the control shaft will rotate. Thus, the electrical output of the potentiometer is controlled by the extent to which the trigger is pressed, thereby controlling the rate at which the motor and the device operate. Coiled around a trigger pivot pin 38 is a spiral torsion spring (not shown) that spring loads the trigger so that the latter is maintained in a power-off position when released. One end of the spring is fixed to the trigger and the other end is fixed to the device housing.

Figure 4:
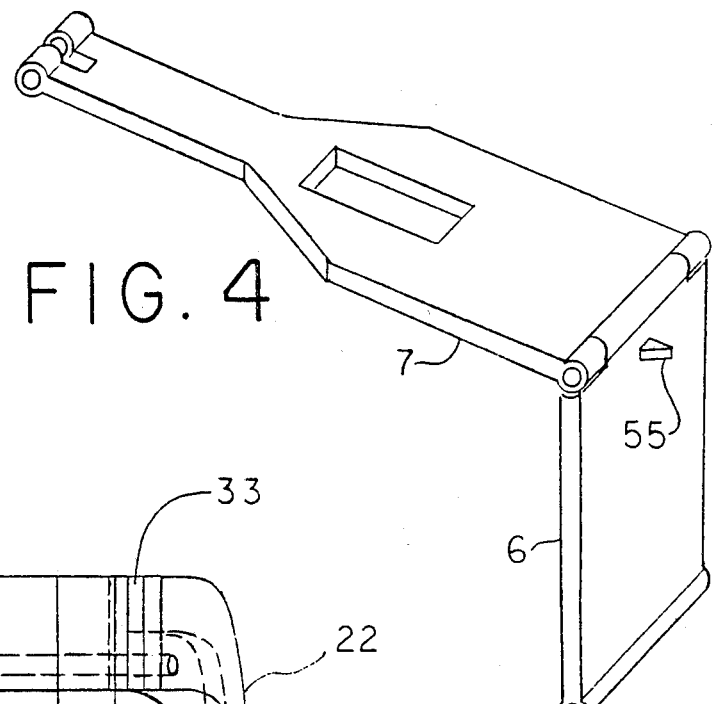
FIG. 4 is an expanded perspective view of the link arm and pawl used in the flossing device.
Figure 5:
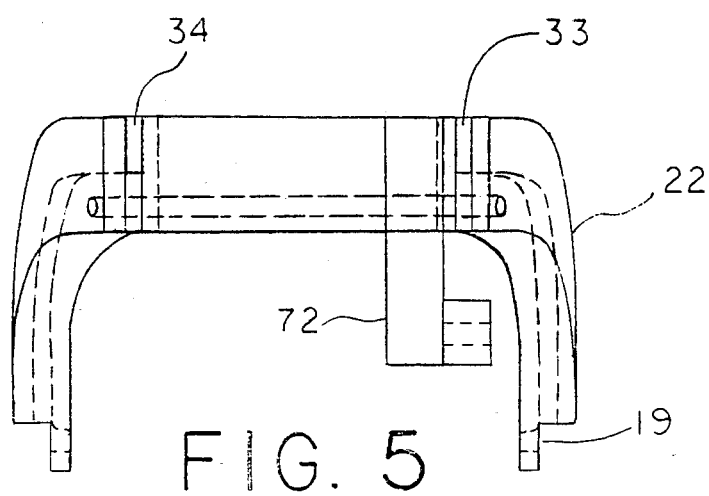
FIG. 5 is an expanded, elevated end view of the inner fork used in the flossing device.
Figure 1:
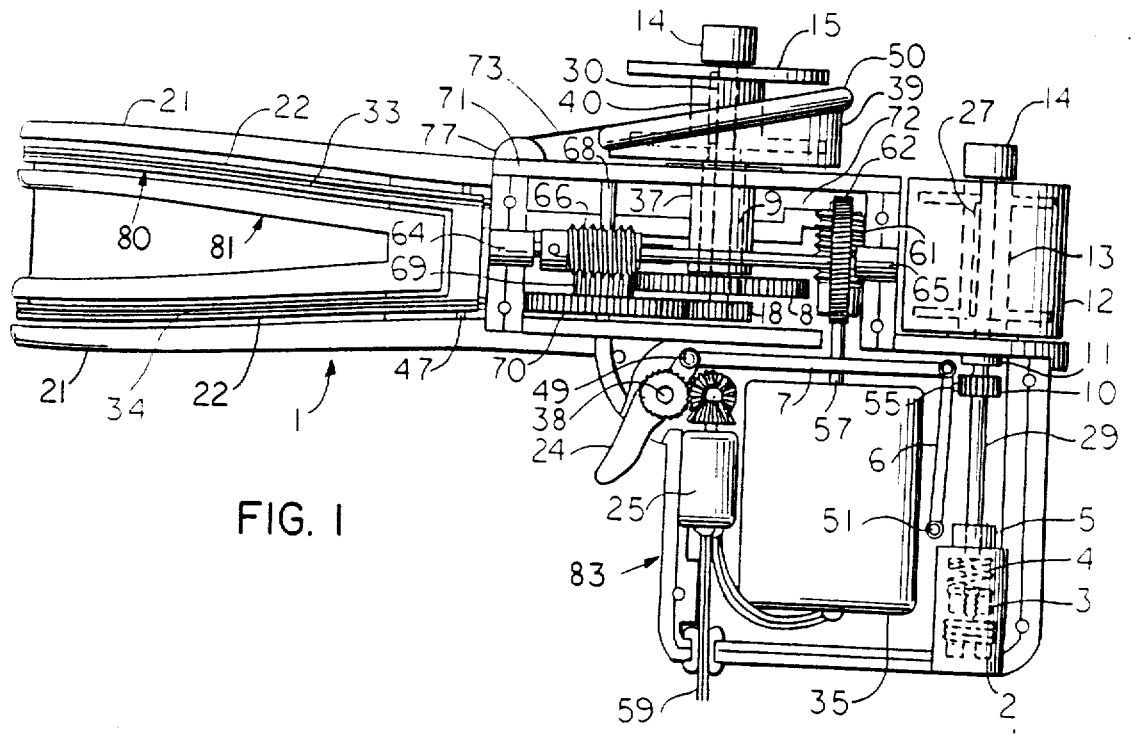
Figure 2:
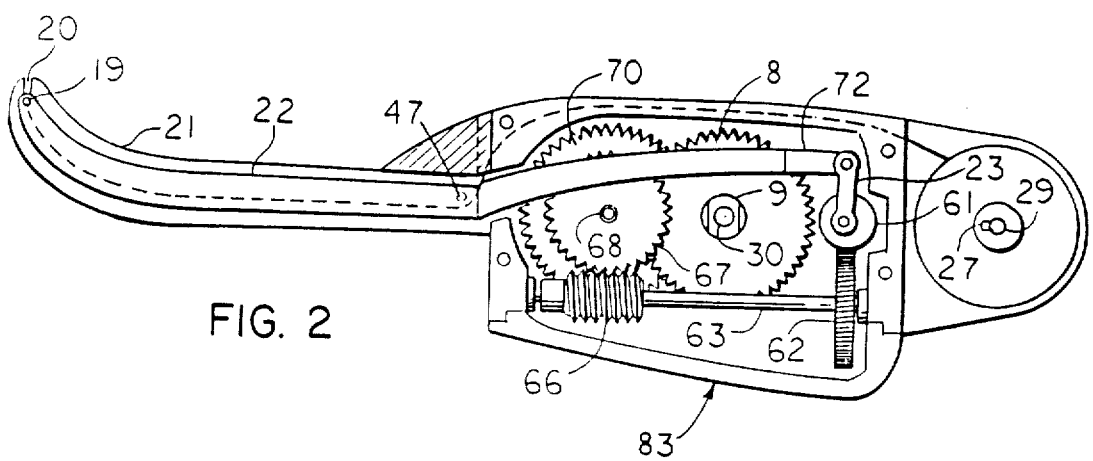
Figure 3:
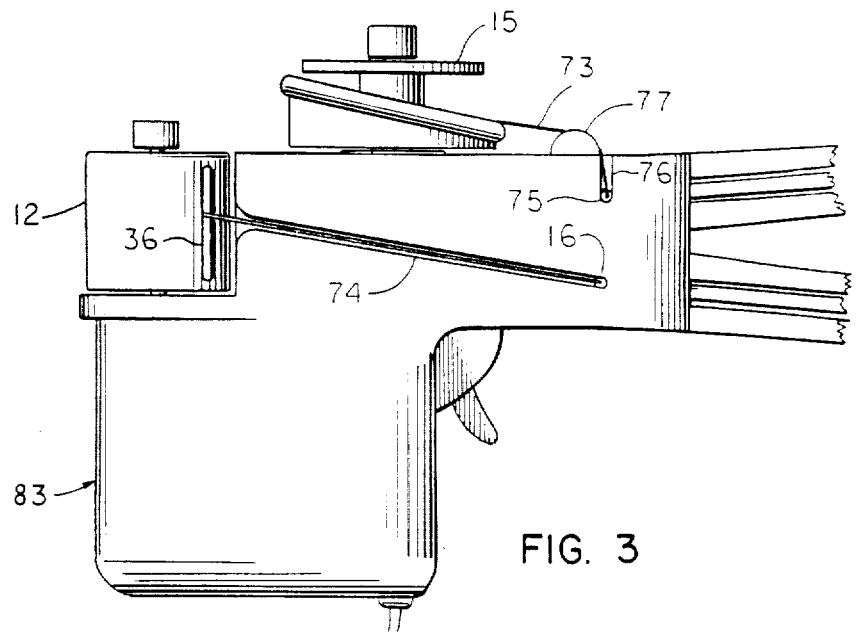
Figure 4:
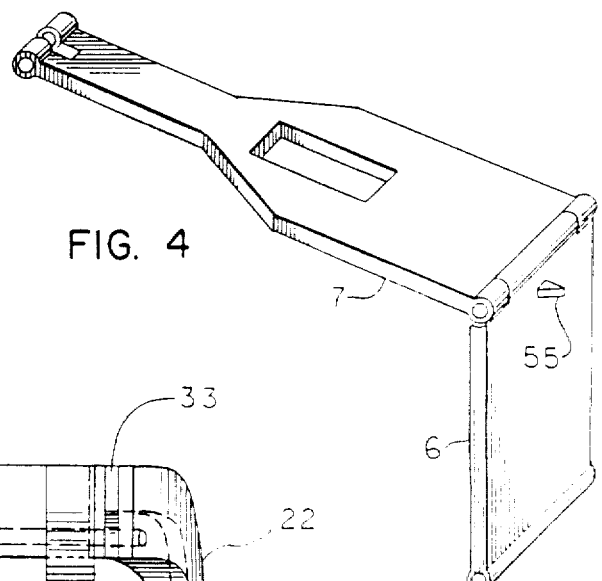
Figure 5:
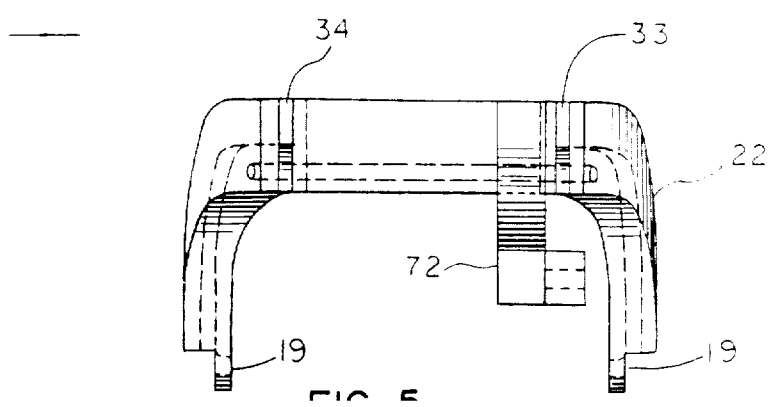

Also slaved to the trigger is a brake system that keeps the dispensing spool immobile while the trigger is not pressed. Components of the brake system include a link arm 7, shown in FIGS. 1 and 4, which has one end portion connected to the trigger by way of a movable joint 49. Another movable joint, on an opposite end portion of the link arm, connects to one end portion of a pawl 6. An opposite end portion of the pawl is disposed to pivot around a pin 51 which is inserted in the housing of the device handle. An opening in the middle of the link arm 7 allows the motor shaft to pass through unobstructed.

When the trigger is released, the force of the trigger spring presses the pawl against a ratchet wheel 10 which is fixed to shaft 29. A tooth 55 projecting from the pawl 6 engages with the wheel and prevents the shaft 29 and dispensing spool 13 from rotating. Thus, no floss can be drawn from the spool; a necessary condition which will be explained hereinafter.

An end portion of the shaft 29 terminates in a drag assembly. A bearing 5, at the interior end of a housing of the drag assembly along with bearing 11, provides support for the rotatable shaft. Within the housing is a disk 3 which is fixed to the shaft. The disk is pressed against a helical spring 4 by an adjustable screw 2. Friction, resulting form the pressure, produces the drag effect.

The purpose of the drag is twofold:
(1) To keep the floss taut as it is drawn throughout the device.
(2) To allow the floss to slacken if the floss segment that spans the inner fork is applied to dental tissues with excessive force while the device is operating.

When the device operates, the floss that spans the inner fork tines moves from one tine to the other. Simultaneously, the floss span reciprocates in a driection perpendicular to the span line. Applied to dentition surfaces, this two dimensional conbination of motions provides a highly effective cleaning process. The rapid vertical motion in concert with the continually changing floss surface, provided by the slower transverse motion, will efficiently loosen and remove deposits. As clean dry floss is constantly fed to the target surface, the freed debris is carried off in and on the used floss. These actions are especially needed on dentition surfaces inside the free gingiva where they will dislodge adhering material and carry the particles out of the sulci.

Since the transverse motion of the floss is slow, the only rapid motion is substantially perpendicular to the gingival surface with which it comes in contact. This eliminates the need for any rapid sawlike motion across soft tissues; a safety consideration. Keeping the drag minimal can also contribute to the safety of this device.

With a finger on the trigger, the user can start, stop, and control the operation speed. The user will draw the floss, that spans the fork, into the spaces between his teeth. Where there is resistance, such as at points where there is tight tooth to tooth contact, he can draw the floss through with the power off (trigger released). In doing so, the brake associated with the dispensing spool, will prevent the floss from slackening. He can then, press the trigger and clean the mesial and distal areas of the teeth by applying light pressure. The surfaces can be cleaned down to (or up to) the attached gingiva.

When finished flossing, the user can simply rinse the forks under hot tap water. The design of the tines allows the running water to pass between them to rinse their surfaces.

The device can be stored with the floss spools in place so the spools need not be remounted with each use.

Versions of the flossing tool can be devised that would be less expensive to produce. One version of the instrument could meet some of its intended objectives without the level-winding feature of the floss retrieval system. This would involve elimination of rail 50, rail support cup 39, first bearing 9, second bearing 37, first gear 18, second gear 8, fourth gear 67, fifth gear 69, sixth gear 70, and second shaft 68 with its bearings. A fixed bearing would receive a journaled portion of spindle shaft 30. Second worm 66 and first shaft 63 would be positioned to engage a gear coaxially fixed to spindle shaft 30.

It is understood that the preceding description is given merely by way of illustration and not in limitation of the invention and that various modifications may be made thereto without departing from the spirit of the invention as claimed.

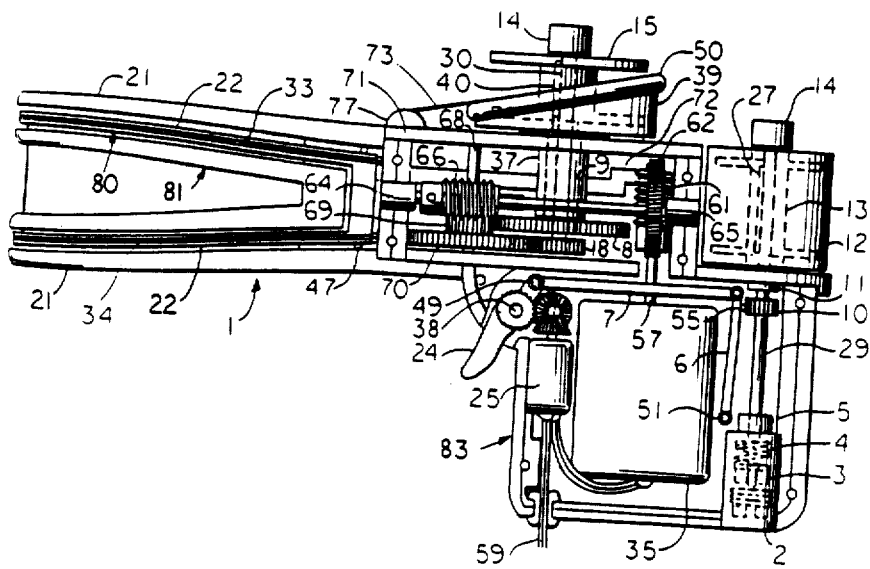

What I claim is:
1. A dental flossing tool comprising:
a housing;
an inner fork pivotally supported on the housing and having two tines which receive teeth to be cleaned therebetween, each tine having guides for guiding the transfer of dental floss from a distal end portion of one tine to a distal end portion of the opposite tine wherein the floss forms a movable span therebetween;
a dispensing spool rotatably supported on the housing for dispensing a strand of dental floss passing to the fork;
a take-up spool rotatably supported on the housing for retrieving dental floss passing from the fork;
means for reciprocating the fork up and down relative to the teeth;
means for producing continuous rotary motion of a drive shaft;
a speed-reduction gear train drivingly connecting the take-up spool with the drive shaft for continuous slow rotation of the spool; and
floss traversing means cooperative with the speed-reduction gears for traversing the floss across the take-up spool for level-winding to produce a continuous slow and substantially unvarying advancement of the floss strand.

2. The dental flossing tool of claim 1, wherein the floss traversing means comprises a cam rotatably supported encircling the take-up spool and having a common axis with the same, the cam connected with the gear train for simultaneous rotation of the cam and the take-up spool such that the rotation rate of the cam is less than the rotation rate of the spool wherein the cam in contact with the floss compels the same to traverse the spool.

3. The dental flossing tool of claim 2, wherein the cam comprises an elliptically shaped endless rail fixedly mounted at an oblique angle relative to the spool axis.

4. The dental flossing tool of claim 1, further comprising a shield fork rigidly extending from the housing and enclosing inner and outer sides of each tine of the reciprocating inner fork for shielding the same from contact with oral tissues, each shield fork tine being elongated, narrow, and having a curved end portion for convenient access to remote areas within the oral cavity.

5. The dental flossing tool of claim 4, wherein each shield fork tine defines an opening along its length which allows direct access of all surfaces of the shield fork and inner fork to a stream of faucet water for rinsing.

6. The dental flossing tool of claim 1, wherein the gear train comprises:
a first gear fixedly connected to the take-up spool;
a second gear fixedly connected to the traversing means;
a first worm fixedly connected to the drive shaft;
a third gear engaged with the first worm;
a second worm fixedly connected to the third gear;
a fourth gear engaged with the second worm;
a fifth gear engaged with the second gear and fixedly connected to the fourth gear; and
a sixth gear engaged with the first gear and fixedly connected with the fourth and fifth gears.

7. The dental flossing tool of claim 1, further comprising a protective shell enclosing the dispensing spool for preventing contamination of floss on the spool, the shell having a slot-like opening positioned parallel to the axis of the spool for allowing floss to be drawn therefrom, the spool and shell detachable as a unit.

8. A dental flossing tool comprising:
- a housing;
- an inner fork pivotally supported on the housing and having two tines which receive teeth to be cleaned therebetween, each tine having guides for guiding the transfer of dental floss from a distal end portion of one tine to a distal end portion of the opposite tine wherein the floss forms a movable span therebetween;
- a dispensing spool rotatably supported on the housing for dispensing a strand of dental floss passing to the fork;
- a take-up spool rotatably supported on the housing for retrieving dental floss passing from the fork;
- means for reciprocating the fork up and down relative to the teeth;
- means for producing continuous rotary motion of a drive shaft;
- a speed-reduction gear train drivingly connecting the take-up spool with the drive shaft for continuous slow rotation of the spool;
- floss traversing means cooperative with the speed-reduction gears for traversing the floss across the take-up spool for level-winding to produce a continuous slow and substantially unvarying advancement of the floss strand;
- a ratchet wheel fixedly connected to the dispensing spool;
- a trigger switch pivotally mounted to the housing and movable between an ON position and an OFF position; and
- a pawl operatively connected to the switch wherein the pawl engages the ratchet wheel to lock the dispensing spool and the floss span when the switch is in the OFF position so that the floss span can be forced through tight spots between adjacent teeth, the pawl disengaged from the ratchet wheel when the switch is in the ON position.

9. The dental flossing tool of claim 8, further comprising a potentiometer operatively connected to the trigger switch and electrically connected between an electric power source and the means driving the inner fork and drive shaft for adjustable power control of the tool.

10. A dental flossing tool comprising:
- a housing;
- an inner fork pivotally supported on the housing and having two tines which receive teeth to be cleaned therebetween, each tine having guides for guiding the transfer of dental floss from a distal end portion of one tine to a distal end portion of the opposite tine wherein the floss forms a movable span therebetween;
- a dispensing spool rotatably supported on the housing for dispensing a strand of dental floss passing to one of the tines;
- a take-up spool rotatably supported on the housing for retrieving dental floss passing from the opposite tine;
- means for reciprocating the fork up and down relative to the teeth;
- means for producing continuous rotary motion of a drive shaft;
- a speed-reduction gear train drivingly connecting the take-up spool with the drive shaft for continuous slow rotation of the spool;
- floss traversing means cooperative with the speed-reduction gears for traversing the floss across the take-up spool for level-winding to produce a continuous slow and substantially unvarying advancement of the floss strand;
- a disk fixedly connected to the dispensing spool;
- an adjustable screw supported by the housing; and
- a drag spring positioned between the disk and the screw such that the screw and spring impart a selective amount of spring drag on the dispensing spool such that the floss span will safely yieldingly slacken by drawing from the dispensing spool if the span is applied to oral tissues with greater than a predetermined amount of force, thereby protecting soft tissues.

* * * * *

UNITED STATES PATENT AND TRADEMARK OFFICE
CERTIFICATE OF CORRECTION

PATENT NO. : 4,586,521

DATED : May 6, 1986

INVENTOR(S) : Charles L. Urso

It is certified that error appears in the above-identified patent and that said Letters Patent is hereby corrected as shown below:

The title page should be deleted to appear as per attached title page.

Figures 1-5 should be deleted to be replaced with figures 1-5 as shown on the attached sheets.

Title page, Under "References Cited", Patent No. "4,327,740" should be --4,307,740--.

Column 1, line 27, "task" should be --tasks--.

Column 4, the formula "number of windings per layer = rotational rate of the spool twice the rotational rate of the elliptical rail" should be --number of windings per layer = $\dfrac{\text{rotational rate of the spool}}{\text{twice the rotational rate of the elliptical rail}}$--.

Signed and Sealed this

Thirty-first Day of May, 1988

Attest:

DONALD J. QUIGG

Attesting Officer

Commissioner of Patents and Trademarks

United States Patent [19]

Urso

[11] Patent Number: 4,586,521
[45] Date of Patent: May 6, 1986

[54] MULTI-MOTION DENTAL FLOSSER

[76] Inventor: Charles L. Urso, 215 Newton St., Waltham, Mass. 02154

[21] Appl. No.: 558,826

[22] Filed: Dec. 7, 1983

[51] Int. Cl.⁴ .............................. A61C 15/00
[52] U.S. Cl. ............................... 132/92 R
[58] Field of Search ..................... 132/92 R, 91

[56] References Cited

U.S. PATENT DOCUMENTS

| | | | |
|---|---|---|---|
| 3,759,274 | 9/1973 | Warner | 132/92 R |
| 4,326,549 | 4/1982 | Hinding | 132/92 R |
| 4,327,740 | 12/1981 | Florindez et al. | 132/92 R |
| 4,458,702 | 6/1984 | Grollimund | 132/91 |

*Primary Examiner*—Robert Peshock

[57] ABSTRACT

A dental hygiene device for cleaning between teeth wherein dental floss is advanced, across a span between the tines of a fork, to a motorized level-winding take-up spool. The fork is reciprocated by the motor, resulting in two-dimensional movement of the floss within the span. The moving fork is shielded to prevent contact with oral tissues. Motor speed is varied by a potentiometer operated by way of a trigger. The floss span can be held taut, during passage between tightly contacting teeth, by a brake operated by way of the trigger. An adjustable drag connected to a contamination protected dispensing spool controls floss tension.

10 Claims, 5 Drawing Figures